(12) United States Patent
Müller

(10) Patent No.: US 6,470,069 B1
(45) Date of Patent: Oct. 22, 2002

(54) METHODS, APPARATUSES AND IMAGING MODE FOR TOMOGRAPHIC IMAGING

(75) Inventor: Timo Müller, Espoo (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 09/700,663

(22) PCT Filed: Jun. 23, 1999

(86) PCT No.: PCT/FI99/00556

§ 371 (c)(1),
(2), (4) Date: Nov. 17, 2000

(87) PCT Pub. No.: WO00/00085

PCT Pub. Date: Jan. 6, 2000

(30) Foreign Application Priority Data

Jun. 26, 1998 (FI) ................................................. 981475

(51) Int. Cl.⁷ ............................................... G01N 23/00
(52) U.S. Cl. ........................................... 378/21; 378/38
(58) Field of Search ............................... 378/21, 38, 39

(56) References Cited

U.S. PATENT DOCUMENTS

| | | | |
|---|---|---|---|
| 4,039,837 A | 8/1977 | Ohta et al. ............... 250/445 T |
| 4,852,134 A | 7/1989 | Kinanen et al. ............... 378/38 |
| 4,985,907 A | 1/1991 | Moteni ........................ 378/139 |
| 5,012,501 A | 4/1991 | Palonen et al. ................ 378/39 |
| 5,093,852 A | 3/1992 | Nishikawa et al. ............ 378/39 |
| 5,325,415 A | 6/1994 | Coffman ....................... 378/38 |
| 5,371,775 A | 12/1994 | Kanerva et al. ............... 378/38 |
| 5,425,065 A | * 6/1995 | Jarvenin ....................... 378/40 |
| 5,732,119 A | * 3/1998 | Kopsala ........................ 378/26 |
| 5,793,837 A | * 8/1998 | Mezhinsky et al. ............ 378/38 |
| 5,921,927 A | * 7/1999 | McArdle ...................... 600/425 |
| 6,018,563 A | * 1/2000 | Arai et al. ..................... 378/39 |
| 6,173,035 B1 | * 1/2001 | Tachibana et al. ............ 378/39 |

* cited by examiner

Primary Examiner—David P. Porta
Assistant Examiner—Irakli Kiknadze
(74) Attorney, Agent, or Firm—Nixon & Vanderhye P.C.

(57) ABSTRACT

This invention relates to tomographic imaging and is particularly intended to be applied to medical x-ray photography. An object of the invention is to provide an imaging mode where the imaging means can follow the anatomy of the object to be imaged without having to make compromises between the thickness of the layer to be imaged and the optimal imaging path, i.e., a path which is perpendicular to the object to be imaged. The invention provides a new way of producing tomographic effect in tomographic methods based on the use of a narrow beam, the new way being based on the idea that the rotational direction of the beam is changed in the object to be imaged during an imaging scan.

36 Claims, 9 Drawing Sheets

METHODS, APPARATUSES AND IMAGING MODE FOR TOMOGRAPHIC IMAGING

BACKGROUND AND SUMMARY OF THE INVENTION

This invention relates to methods, apparatuses and an imaging mode for tomographic imaging, particularly for medical x-ray imaging, according to the preambles of the accompanying independent claims.

Imaging methods utilizing electromagnetic radiation can be divided into two groups: radioscopic methods and tomographic methods. in traditional radioscopy the radiation source, the object to be imaged and the radiation detector, e.g. an x-ray film, are stationary with respect to one another during the imaging session. Imaging methods in which a narrow beam is moved over the object to be imaged are also known.

Tomographic methods can be divided into linear (i.e. planar) tomographic methods and complex motion or spiral tomography methods. In tomographic imaging the object to be imaged and/or the radiation detector are moved with respect to each other in a controlled manner, and thus in linear tomography the tomographic movement occurs with respect to one axis and in complex motion tomography with respect to two axes. These methods use a beam which is of the same size as the object to be imaged, and the object is usually held in place as the radiation source and radiation detector are moved dependently on each other on the opposite sides of the object to be imaged in the opposite directions so that the beam penetrates the object from different directions, but its centre of movement/rotation in the object does not move. The methods provide accurate images of the imaging area in the centre of rotation of the beam, whereas the other parts of the object are blurred partially or totally.

There are also 'narrow beam tomography' methods in which a beam considerably narrower than the object to be imaged sweeps across the area to be imaged and the beam is turned with respect to the object to be imaged. In that case the imaging means (radiation source and radiation detector) must be moved in a controlled manner so that the detector moves in relation to the beam at a lateral velocity which corresponds to the perpendicular sweeping speed of the beam in the area to be imaged multiplied by the ratio of magnification, i.e. by a coefficient which is the ratio of the distance of the beam focus (=radiation source) and the distance of the focus from the area to be imaged. Here the term detector refers to a film or the like; in digital imaging, for example, the movement of the detector with respect to the area to be imaged may be replaced with a suitable electrical function, such as charge transfer on the surface of a semiconductor sensor.

Tomographic methods are commonly used in different fields of medicine, e.g. in odontology. Linear and spiral tomography methods have been employed e.g. for cross-sectional imaging of the dental arc, and narrow beam tomography e.g. for producing panoramic images of the dental arc. Here a panoramic image refers to imaging of the dental arc onto a plane by moving the imaging area of imaging means along a path resembling the shape of the dental arc and keeping the imaging means substantially perpendicular to the dental arc during the whole imaging session.

Prior art tomographic solutions are described e.g. in U.S. Pat. Nos. 4,039,837; 4,985,907; 5,012,501 (priority FI 894339) and U.S. Pat. No. 5,371,775 (priority FI 922361). It is known to produce a tomographic effect by turning the imaging means in a certain direction and by simultaneously moving them with respect to the area to be imaged so that either this area remains in the physical centre of rotation of the suspension arm in the imaging means or it is left outside the centre of rotation. In the latter case the physical supporting point of the suspension arm in the imaging means can be moved along a path with the shape of an arc by simultaneously turning the suspension arm so that the beam constantly hits the tangent of the curved path of the supporting point in the perpendicular direction, and thus the area to be imaged is the centre of rotation of the curved path. There are also solutions in which the suspension means of the radiation source and the detector are provided with different degrees of freedom to move and solutions in which the radiation source is switched off during one imaging session, moved to another starting point and radiation is started again by rotating the imaging means in the previous direction or in the opposite direction. There are also solutions in which the beam sweeps across the area to be imaged in one direction and returns in the opposite direction and solutions in which the linear direction of movement of the rotation centre of the imaging means is turned during the imaging session.

One restriction of the prior art solutions is that the object itself imposes limitations on the ways in which it can be imaged by these methods. The layer thickness to be projected onto the detector is influenced by the turning angle of the beam in the object to be imaged, the angle being partially dependent on the anatomy of the object to be imaged. For example, when a narrow beam is used for imaging a straight object, the result may be a nondesirable X-ray image.

The problem associated with the use of a wide beam is that it is necessary to use radiation detectors with a large surface area. The need for a large surface area restricts the use of digital detectors which are relatively expensive, their price being proportional to their surface area.

Considering simplicity of the suspension structure of the imaging means, it would be preferable to keep the detector perpendicular to the beam during the whole imaging session, but if a beam of the same size as the object to be imaged is used, the resolution of the imaging result will not be optimal in this case. When a narrow beam is employed, the error resulting from this is insignificantly small.

In narrow beam tomographic methods, in which the imaging process is based on the sweep of a narrow beam across the object and which thus allow the use of detectors with a small surface area, the use of digital detectors is also economically feasible. In fact, it would be desirable to find new solutions to the problems related to the general limitations of the prior art narrow beam tomography methods.

Devices intended for different tomographic methods have conventionally been produced for a certain tomographic method. However, the present trend is to develop solutions which allow to use one device for various purposes, i.e. the goal is to be able to use the same device in different tomographic methods and for imaging different projections. For example, forming of beams of different sizes and defining their size as desired before supplying them to the detector have proven to be challenging problems. Furthermore, production of high-quality tomographic images requires that the detector and/or radiation source of the device should be provided with sufficiently many degrees of freedom to move so that the detector can be kept in the correct direction with respect to the object to be imaged in all imaging modes.

An object of the present invention is to provide a solution which allows to image layers of the desired thickness and shape from different objects by means of one preferred device without complex collimator structures which impose limitations on the beam and without structures which are difficult to implement and comprise several degrees of freedom to move. Another object of the invention is to produce a tomographic effect so that the imaging means can follow the anatomy of the object to be imaged without having to make compromises between the thickness of the layer to be imaged and the optimal imaging path, i.e. a path which is perpendicular to the object to be imaged.

Furthermore, when the same device can be used for implementing different imaging modes according to the invention, investment in imaging sensors based on modern digital technology becomes more profitable, which lowers the threshold of introducing them. Digital technology facilitates the doctors' work, for example, since it does not only allow the doctors to produce better images than earlier and thus to make more accurate diagnoses, but also to store the images and manage the images in electronic form, together with all other documents related to the patient.

To achieve the objects of the invention, a new way of producing a tomographic effect has been developed for tomographic methods based on the use of a narrow beam. The invention is based on the idea that the direction of rotation of the beam is changed in the object to be imaged during an imaging scan, and thus creation of the tomographic angle (different directions from which the beam penetrates the object to be imaged), which affects the thickness of the layer to be imaged, can be arranged as a separate function. This can be preferably implemented e.g. in a method known per se, in which the object to be imaged is held in the physical centre of rotation of the imaging means, at the suspension arm of the imaging means, at the opposite ends of which the radiation source and the detector are located, is moved along the object to be imaged (linear movement) as the detector, e.g. a film, is moved in the opposite direction with respect to the movement of the arm at a speed which corresponds to the beam speed in the area to be imaged multiplied by magnification. In that case the centre of rotation of the arm moves at the speed of the arm's linear movement regardless of the direction in which the suspension arm of the imaging means is turned (the tomographic effect is produced by turning the arm). By rotating the suspension arm to and fro in the desired manner during the scanning motion a tomographic image with the desired thickness dependent on the tomographic angle can be produced even from a straight object.

The method of the invention can be applied in several prior art methods, e.g. in the method disclosed in the above-mentioned U.S. Pat. No. 4,039,837 for imaging a curved object. In that case the suspension arm of the imaging means is moved according to the prior art so that the centre of rotation is at the object to be imaged and the beam is perpendicular to the tangent of the curve of the object, and thus a narrow beam tomographic image which is known from panoramic imaging and dependent on the radius of curvature of the object is obtained. If the radius of curvature is large, the tomographic angle will be small when a narrow beam is used, and as a result, the layer to be imaged will be too thick. Instead, by changing the direction of rotation of the suspension arm of the imaging means according to the invention, the tomographic effect can be increased, and thus the thickness of the layer to be imaged can be chosen as desired. The invention allows tomographic imaging of an anatomy of any shape, i.e. the object may be curved in one or two directions, straight or a combination of these.

More precisely, characteristic features of the invention are described in the characterizing parts of the appended independent claims.

In the following the invention and its application will be described by examples with reference to the accompanying drawings.

DETAILED DESCRIPTION OF THE DRAWINGS

Figure 1:
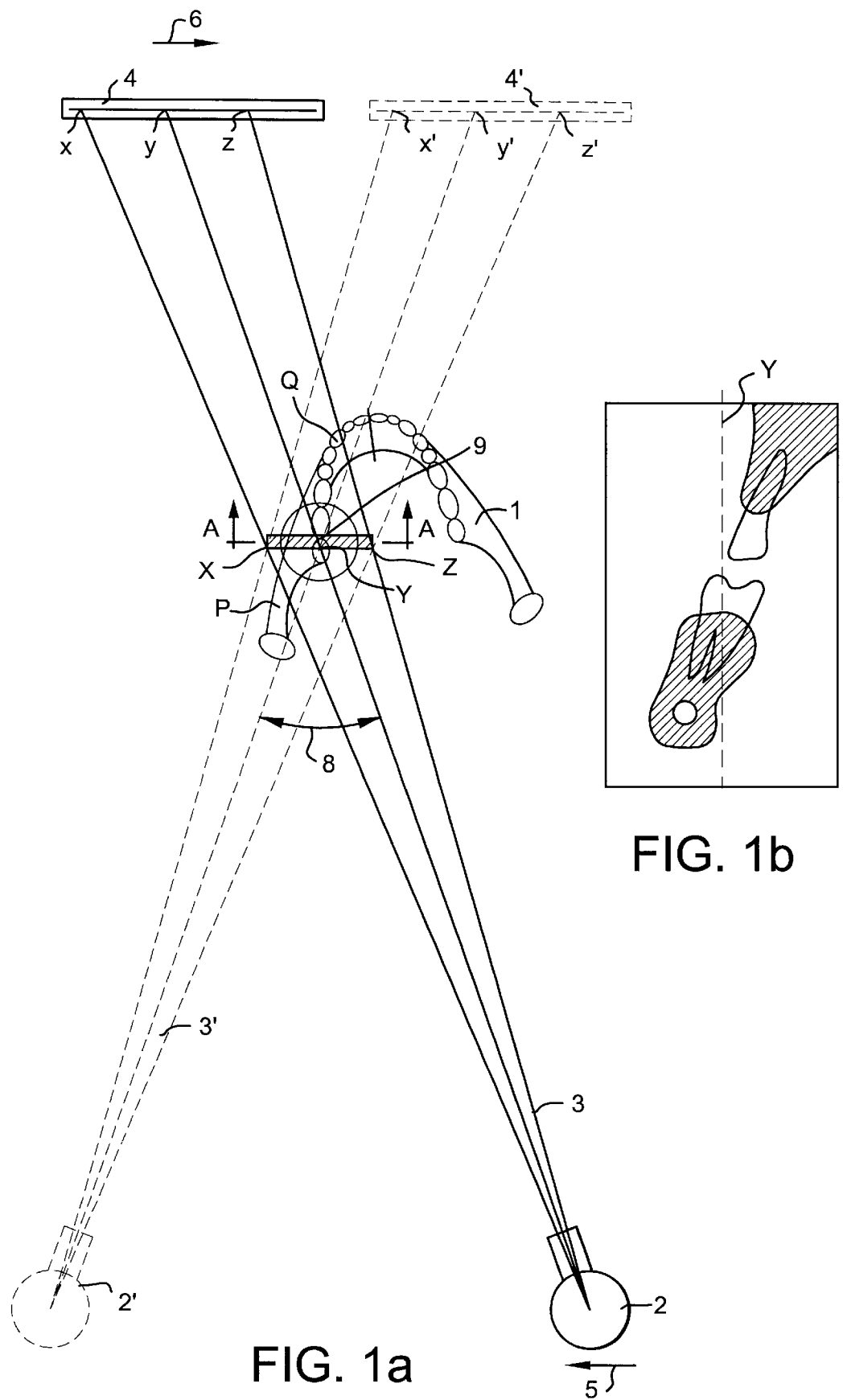
FIG. 1A and its cross-sectional FIG. 3B illustrate principles of prior art tomographic imaging with a beam of the same size as the object to be imaged.

FIGS. 1A and 1B illustrate principles of prior art tomographic imaging with a beam of the same size as the object to be imaged. In the linear tomography method of FIG. 1A a beam (3, 3') obtained from a radiation source (2, 2') is directed to an object (1) to be imaged, and radiation that has penetrated the object is measured with a detector (4, 4'). During the imaging session the imaging means, i.e. the radiation source (2, 2') and the detector (4, 4'), are moved by moving the radiation source (2, 2') in one direction (5) and the detector (4, 4') in the opposite direction (6) so that the ratio of the travel speeds is equal to the ratio of the distances of the means (2, 2', 4, 4') from the area (7) to be imaged in the object (1). Thus all points (X, Y, Z) in the area (7) to be imaged are projected onto the same area (x, x', y, y', z, z') of the detector (4, 4') and the sections (P, Q) outside the area to be imaged are constantly projected onto different sections of the detector (4, 4') or completely outside it, in which case they are blurred altogether from the image to be projected onto the detector (4, 4') (FIG. 1B). One factor affecting the layer thickness of the area (7) to be imaged onto the detector (4, 4') is the angle (8), known as the tomographic angle, formed between the initial and final position of the imaging means (2, 2', 4, 4'); the larger the angle (8), the thinner the layer to be projected onto the detector (4, 4') will be.

In practice the tomographic movement according to FIG. 1A can be implemented e.g. by attaching the radiation source (2,2') and detector (4, 4') to the opposite ends of a suspension arm of the imaging means (not shown) and by placing the area (7) to be imaged at the physical fixing point, i.e. centre of rotation (9), of the suspension arm, and thus the imaging conditions are fulfilled automatically as the suspension arm is rotated.

Figure 2:
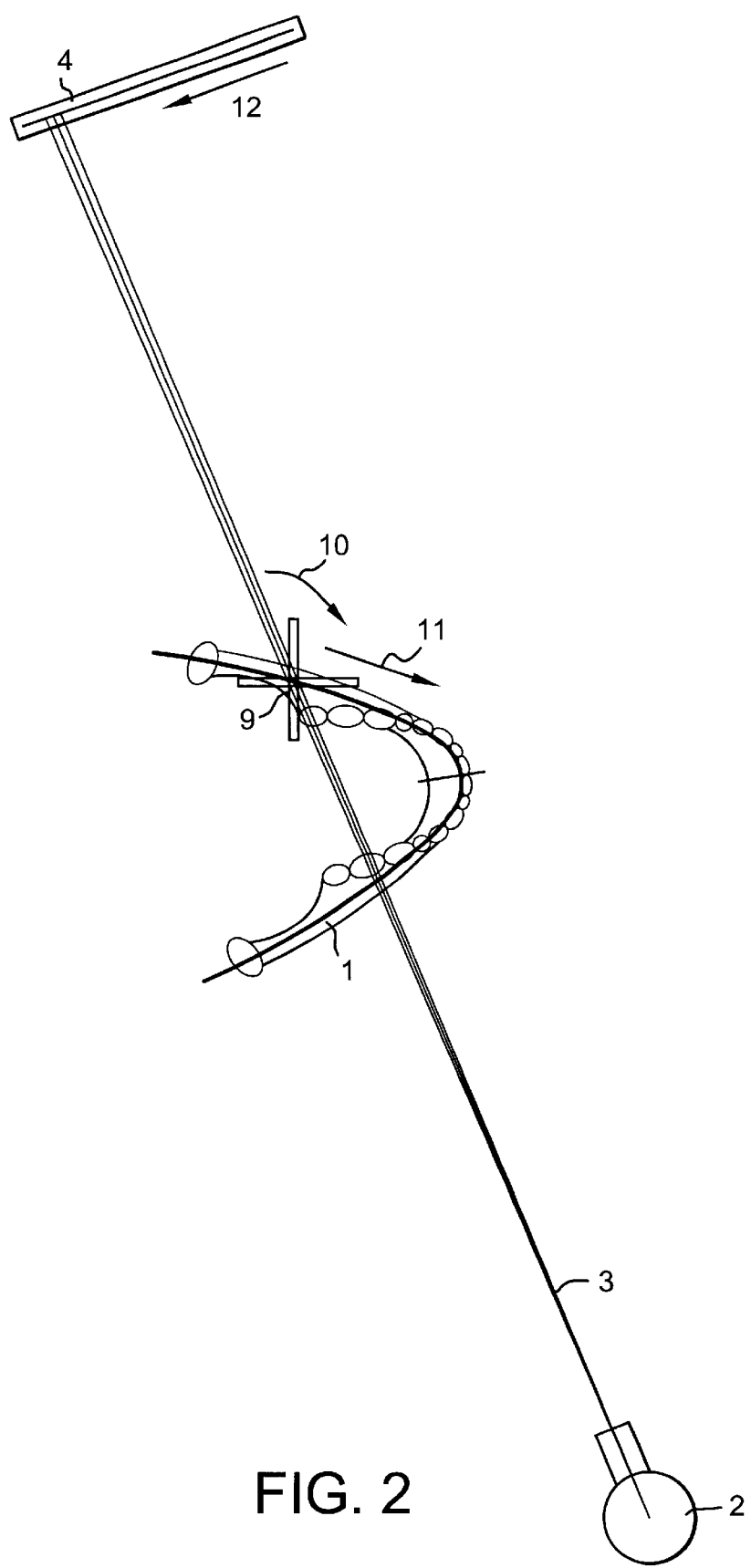
FIG. 2 illustrates principles of prior art tomographic imaging with a narrow beam from a curved object, FIG. 3A and its cross-sectional FIG. 3B illustrate one way of imaging according to the invention with a narrow beam for producing a cross-sectional image.

FIG. 2 illustrates a prior art solution for producing a tomographic image with a narrow beam from a curved object. A beam (3) narrower than the object (1) to be imaged is generated in the radiation source (2) by means directly attached to it or by other means (not shown), such as collimator plates. During the imaging session the imaging means (2, 4) are moved so that the centre (9) of rotation of the rotational movement thus produced is moved along the anatomy to be imaged in the direction (11) of the cross-section to be imaged as the imaging means are rotated in one direction (10) with respect to the object (1) to be imaged. Since in the method a beam (3), which is narrower than the object and moves in the linear (11) and rotational (10) direction, scans the object (1) to be imaged, there must be some way of keeping the detector (4) constantly in the correct position with respect to these movements (10, 11) in a controlled manner. The movement of the radiation source (2) and the detector (4) with respect to each other can be controlled by attaching them to the opposite ends of the same suspension arm; and if a conventional film or the like is used as the detector (4), radiation can be measured according to this prior art solution by moving a film wider than the beam during the imaging scan against (12) the direction (10) of rotation of the imaging means (2, 4) at a speed corresponding to the beam (3) speed in the area to be imaged of the object to be imaged multiplied by magnification. In this case magnification is the ratio of the distance of the beam (3) focus from the detector (4) to the distance of the focus from the area to be imaged.

Figures 3A, 3B:
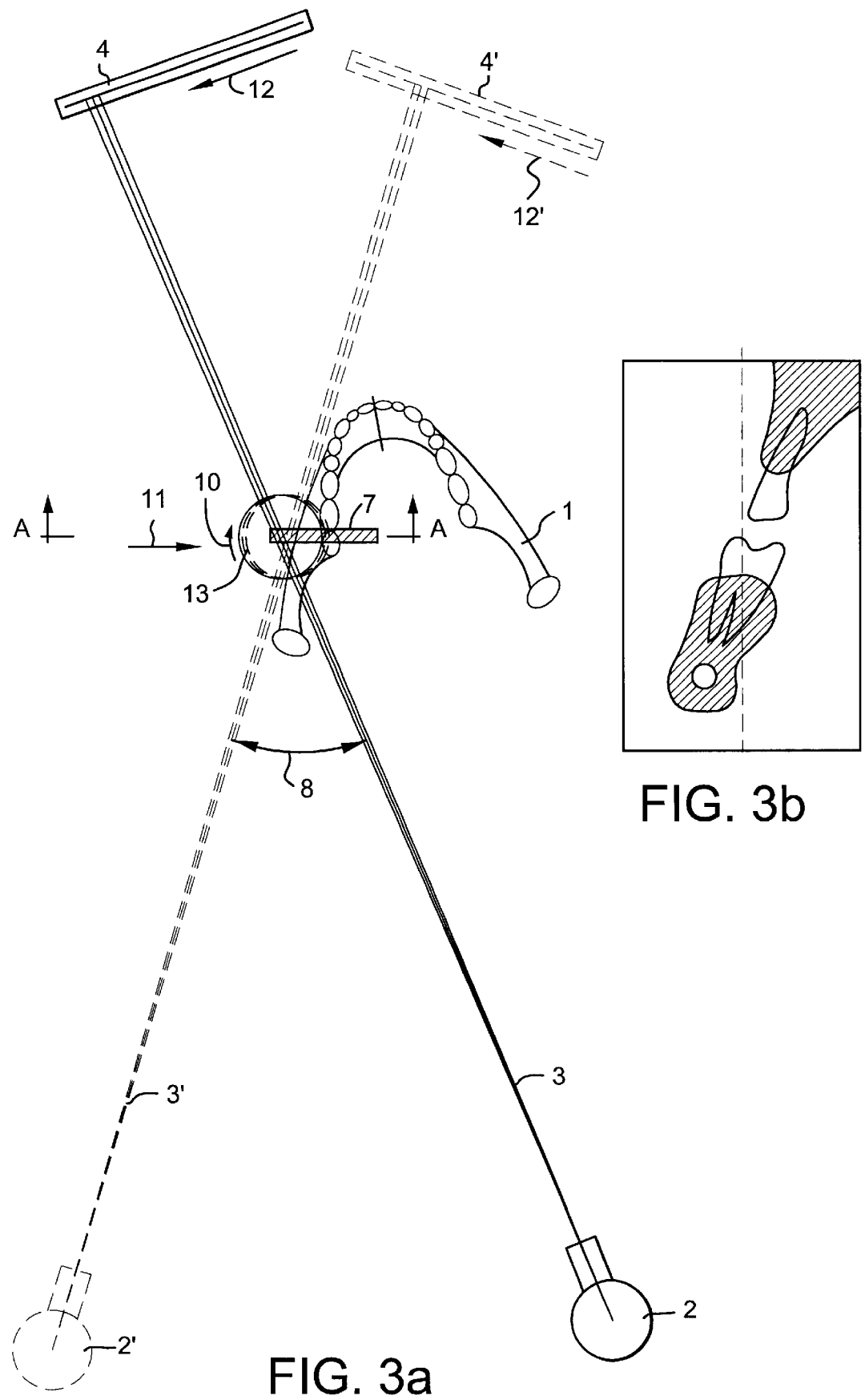

FIGS. 3A and 3B illustrate a method of the invention of producing a tomographic image of a cross section from the object (cf. FIG. 1A). Since the method uses a beam (3, 3') narrower than the object (1) to be imaged, the beam (3, 3') has to scan (11) across the whole area (7) to image the desired area (7) (in FIG. 3A the centre of rotation of the beam has only travelled a short distance in the cross section to be imaged). To produce a tomographic effect according to the prior art, i.e. to image the desired layer thickness, the imaging means (2, 2', 4, 4') would be turned in one direction (10) with respect to the area (7) to be imaged during the imaging scan. According to the present invention, the direction (10) of rotation can be changed (13) during the scanning motion (11), and thus the invention offers new opportunities of influencing the tomographic angle (8) and thus the thickness of the layer to be projected onto the detector (4, 4') from the area (7) to be imaged. The imaging mode of the invention also allows to produce high-quality tomographic images with a narrow beam, and thus it enables the use of reasonably-priced and small-sized digital detectors.

Figure 4:
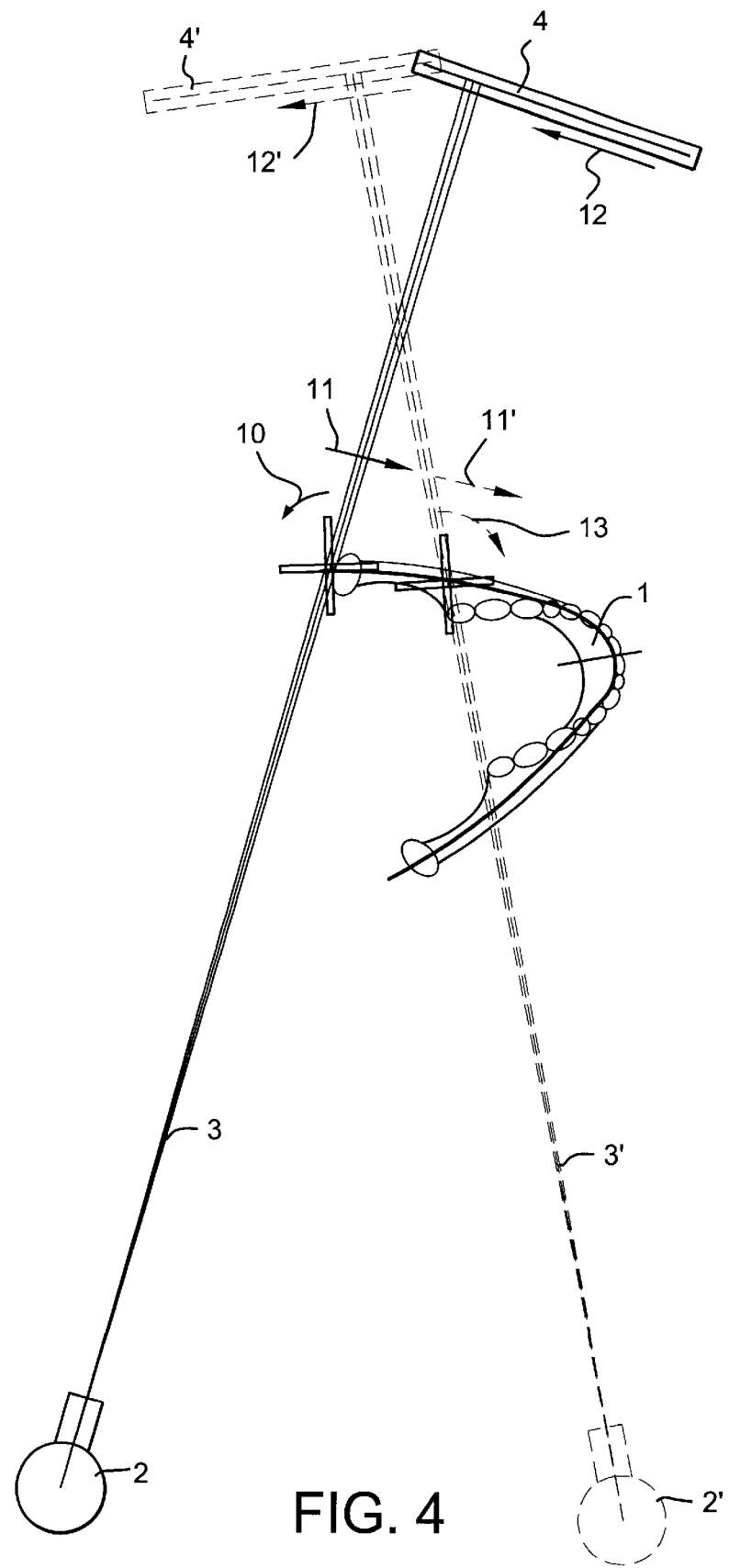
FIG. 4 illustrates use of the invention for panoramic imaging of the dental arc.

FIG. 4 illustrates application of the invention to panoramic imaging of the dental arc, which is known per se. This solution of the invention differs from the method illustrated in FIG. 2 in that the direction (10) of rotation of the imaging means (2, 4) is changed (13) with respect to the object (1) to be imaged e.g. when the beam travels to the area of the dental arc from the area of a temporomandibular joint. The direction of rotation may be changed similarly when the beam travels to the area of the other temporomandibular joint from the area of the dental arc at the final stage of the imaging scan. The imaging method of the invention allows to maintain the incidence angle of the beam in the area to be imaged optimal all the time, i.e. Substantially perpendicular to the area to be imaged, and the thickness of the layer to be imaged can also be optimized.

The method of the invention provides various possibilities of producing different cross sections from the object to be imaged, e.g. different x-ray cross sections of the cranial area. The direction of rotation of the imaging means can be changed within the limits set by the object to be imaged during an imaging scan e.g. only once, constantly during the scan, or over a section of the scan imaging is performed in the conventional manner and in the desired area the direction of rotation is changed with a high frequency. To produce a panoramic image of the dental arc according to the invention the direction of rotation could be changed e.g. five times in the area of both temporomandibular joints or from 1 to 5 times as the beam travels a distance corresponding to its width in the object to be imaged.

Figure 5:
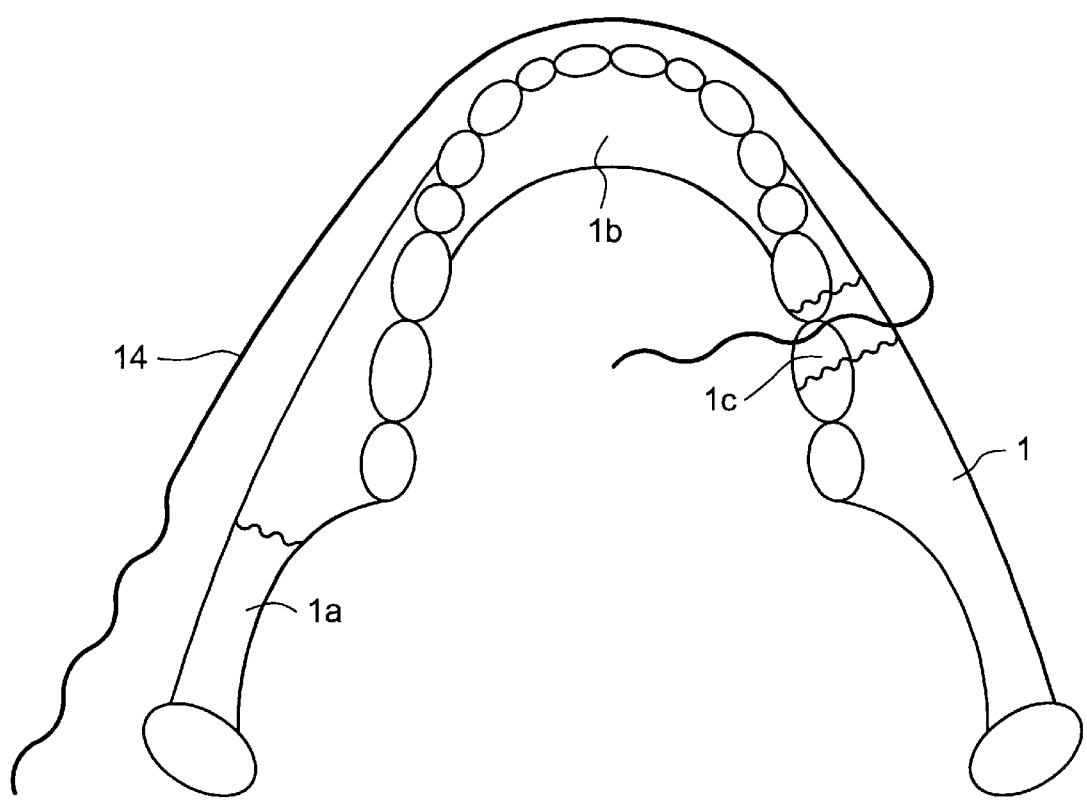
FIG. 5 illustrates use of the invention for obtaining different cross-sectional layers in a controlled manner with one scan of a narrow beam.

In FIG. 5 line (14) around the object to be imaged illustrates the areas (1a, 1b, 1c) of the traditional and the inventive imaging method during an imaging scan, when a thinner longitudinal image is to be produced from the area of the temporomandibular joint than would have been possible with the traditional panoramic imaging method. The imaging scan also includes producing of a cross section from a certain section of the dental arc, and thus all the necessary information on the patient is obtained during a single imaging session. Thus the patient needs to be imaged only once.

Figure 6:
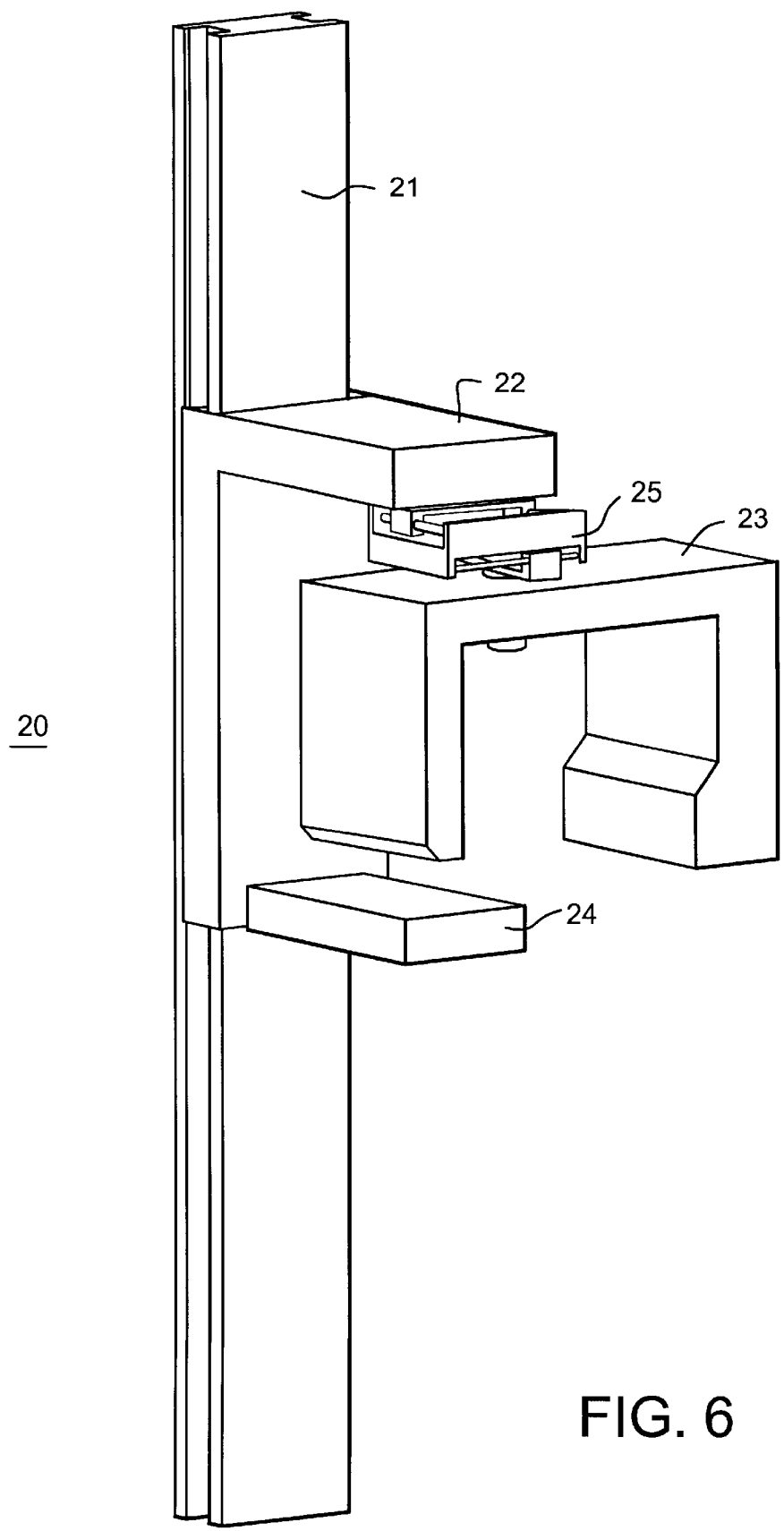
FIG. 6 illustrates a typical prior art apparatus which can be modified for producing tomographic images of the invention with minor changes, FIG. 7A and its cross-sectional FIG. 7B illustrate a device of the invention and its use for producing a cross-sectional image with a narrow beam.

FIG. 6 illustrates an apparatus (20) according to the prior art, which can relatively easily be modified to make it suitable for the method of the invention. This kind of prior art apparatus (20), which is mainly intended for panoramic imaging of the dental arc, consists of a first frame part (21), a second frame part (22) and a third frame part (23). The first frame part (21) may be attached to the floor or wall, in which case it comprises means for altering the height of the second frame part (22). Alternatively, the second frame part (22) may be fixed to the first frame part (21), in which case the first frame part (21) comprises means for adjusting its length (e.g. a telescopic structure). The third frame part (23) functions as a suspension arm of the radiation source and the detector, which are attached to the opposite ends of the suspension arm. The means for positioning the patient in the right place may be arranged in a fourth frame part (24), which may also comprise the control panel of the apparatus.

The second frame part (22) and the third frame part, i.e. the suspension arm (23) of the imaging means, are connected with each other by fixing and moving means (25), which allow the suspension arm (23) to rotate horizontally and move in the x and y directions. The apparatus comprises a system for controlling the movements of the suspension arm (23), which may be implemented e.g. by means of computer-controlled electric motors and guide tracks of the fixing and moving means. The suspension arm (23) may also comprise means for moving the detector in a controlled manner in the horizontal direction.

Figures 7A, 7B:
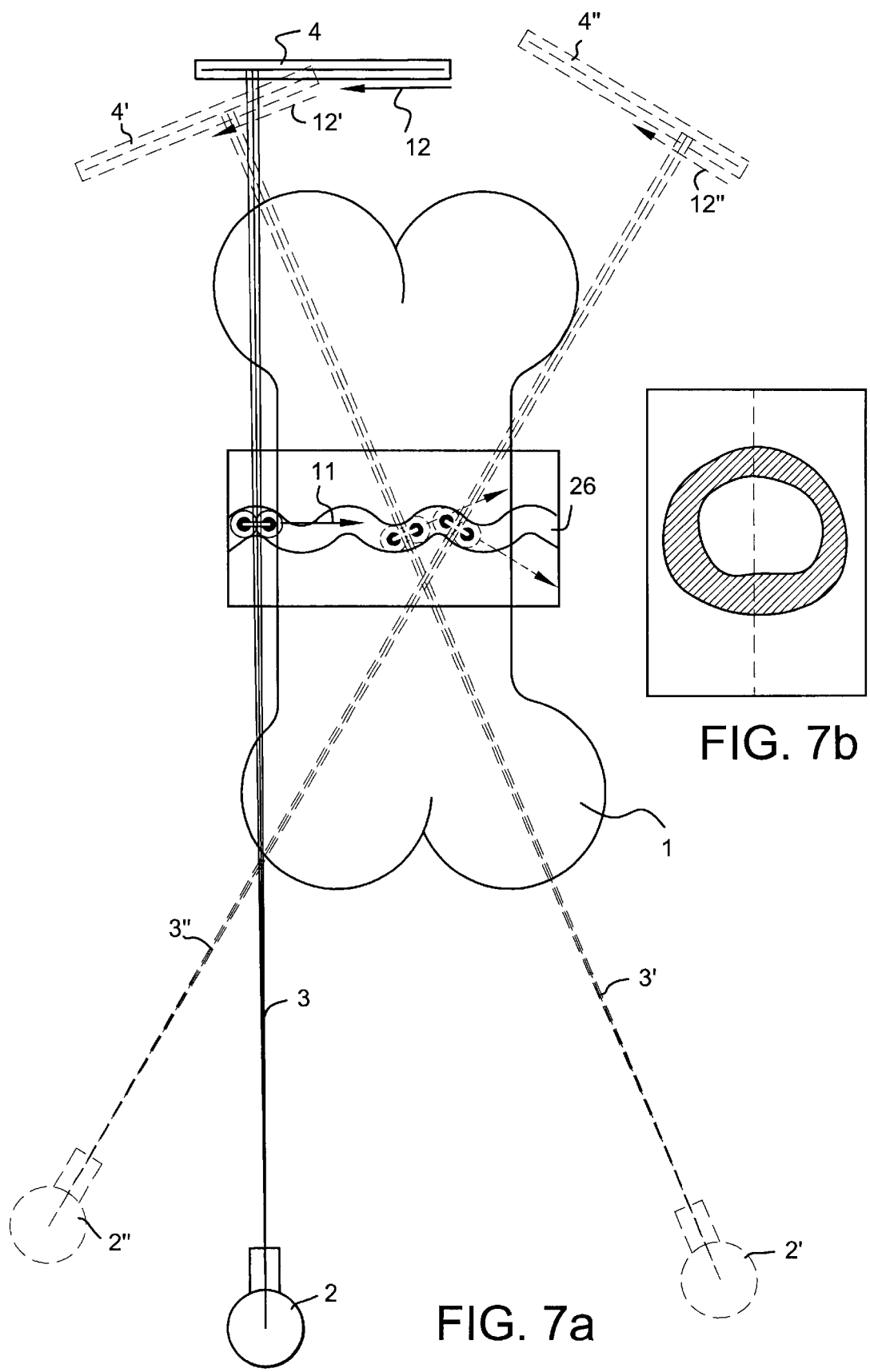

FIG. 7A illustrates one way of modifying the prior art apparatus in accordance with the invention. By providing the track (26) which controls the movement of the suspension arm with one or more S curves in the direction (11) of the cross section to be imaged either over the whole imaging scan or over a desired section of it, e.g. over the area of the temporomandibular joints in panoramic imaging of the dental arc, the direction of rotation of the imaging means changes with respect to the object to be imaged during the scanning motion.

Naturally there are numerous technical ways of implementing the change of the rotational direction according to the invention. Since the different functions of such devices, including motors which drive movable members, can be controlled by a computer program, modification of the control algorithms of the motors is one natural way of making the apparatus suitable for the invention.

Figure 8:
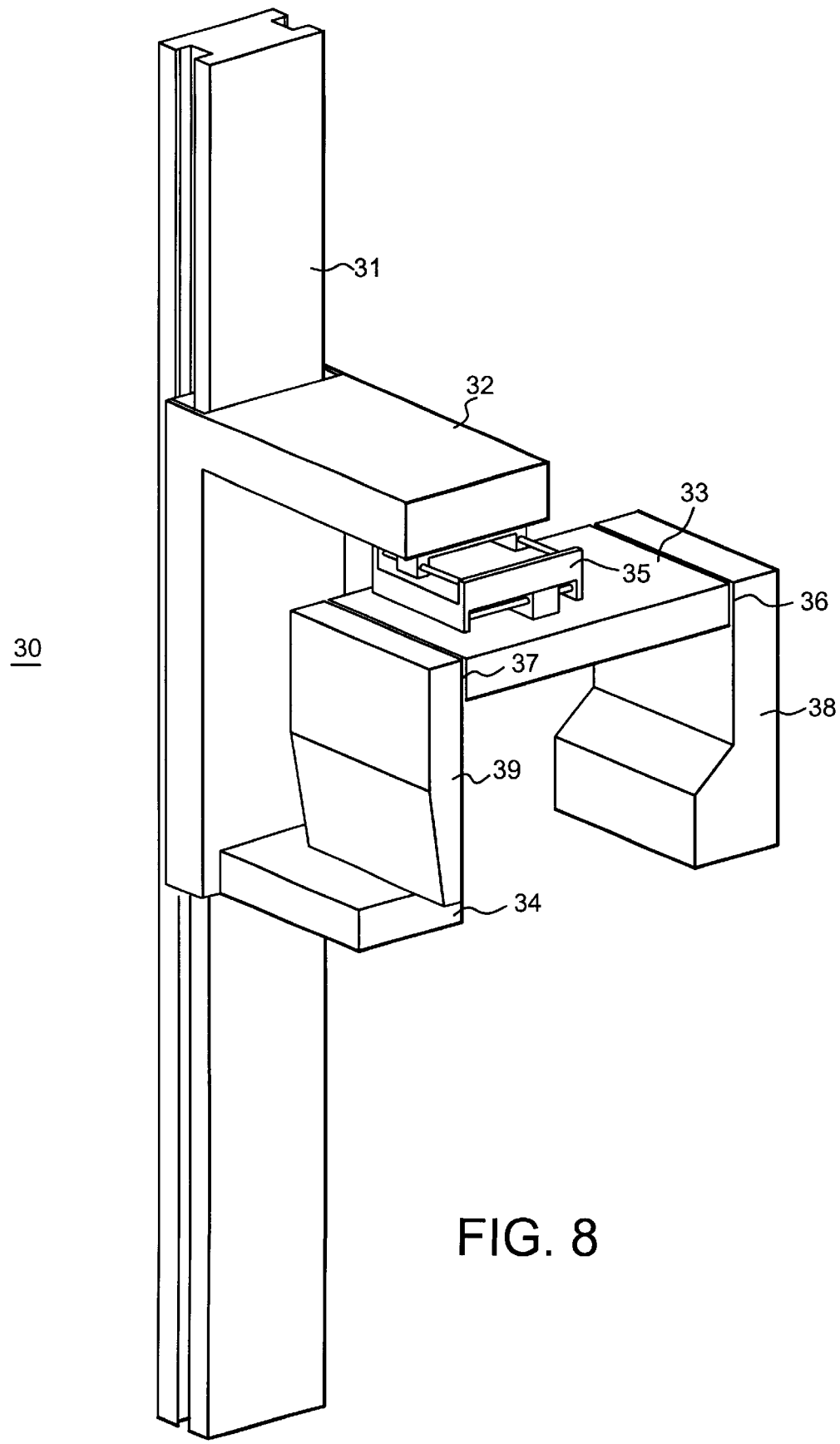
FIG. 8 illustrates a device of the invention, FIG. 9A and its cross-sectional FIG. 9B illustrate yet another way of producing a cross-sectional image with a narrow beam according to the invention.

One possible way of implementing the tomographic method of the invention is to attach the imaging means to the suspension arm so that they can be moved independently, the movements being synchronized electrically or mechanically with each other, from below upwards or from top to bottom with respect to the fixing arm, from left to right or from right to left or both in the horizontal and vertical directions. This structure can also be used for producing the tomographic effect in the vertical direction, which is called 'spiral narrow beam tomography'. For example, the apparatus (20) illustrated in FIG. 6 can be modified so that the apparatus (30) (FIG. 8) consists of the corresponding frame parts (31, 32, 33, 34) and fixing and moving means (35) as the prior art apparatus (20), except that the suspension arm (third frame part) (33) is provided with means (36, 37) for moving the radiation source and/or the detector (38, 39) (or their supporting members) in the vertical direction, too. Thus the vertical degree of freedom to move can be arranged either for both imaging means or only for one of them. In the latter case the counter-movement of this vertical movement can be produced e.g. either by the fixing and moving means (35) between the third (33) and the second frame part (32) or by means for adjusting the height of the second frame part (32) (not shown). Naturally, the fixing and moving means (36, 37) for moving the radiation source and/or the detector (38, 39) (or their supporting members) can be constructed so that either one or both of them produce the horizontal movement or both the horizontal and the vertical movement. Thus the apparatus can be used for complex motion tomographic imaging in various ways.

The imaging means can also be provided with a degree of freedom to move in a manner known per se in the direction of the axis between them, i.e. in the direction of the beam.

Figures 9A, 9B:
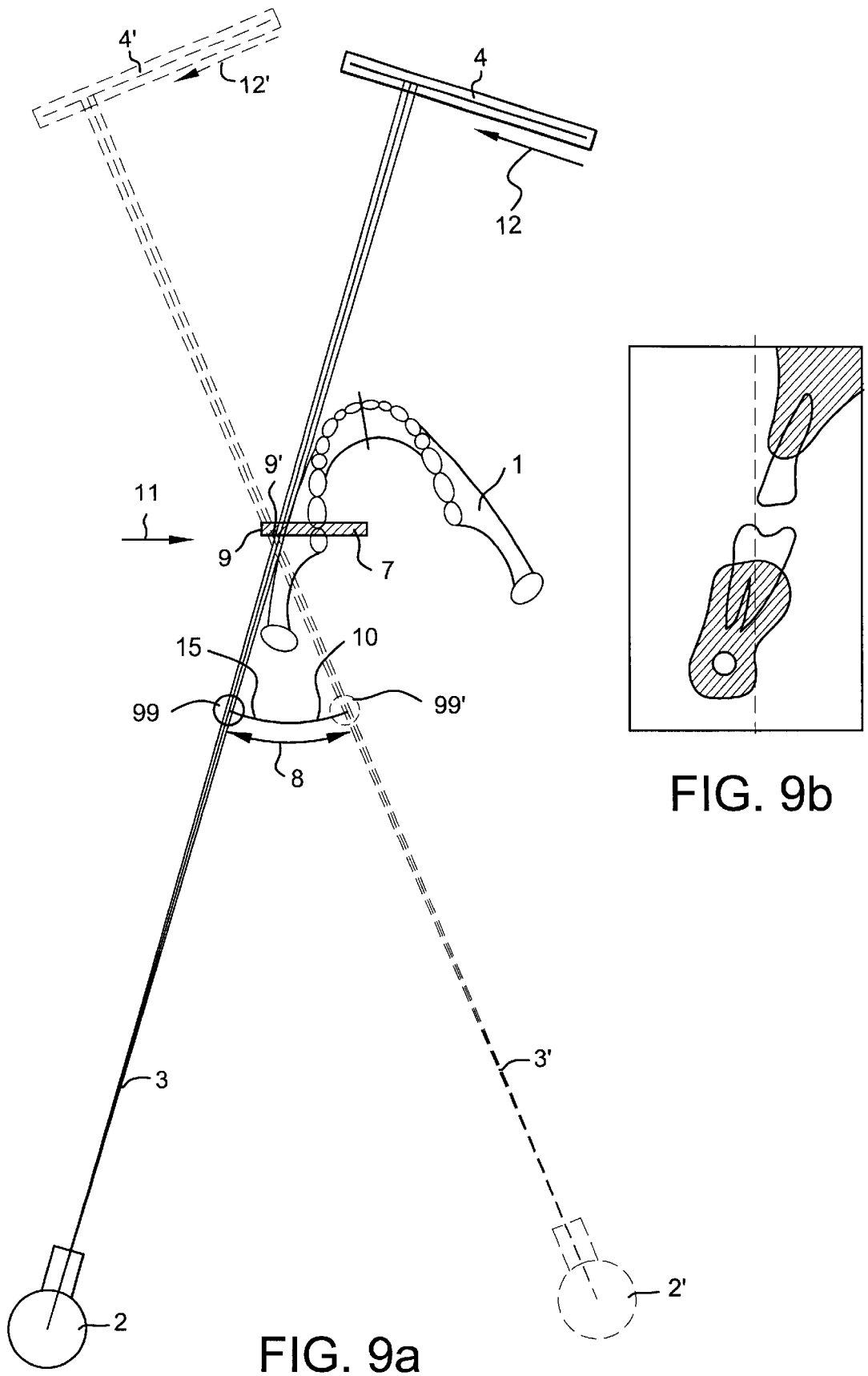

Implementation of the tomographic imaging method according to the invention was described above in an environment where the object to be imaged is located at the physical fixing point of the suspension arm of the imaging means. The inventive tomographic imaging method can also be applied to the method (FIG. 9A) known e.g. from U.S. Pat. No. 5,371,775, where the physical supporting point (99, 99') of the suspension arm of the imaging means (2, 2', 4, 4') is moved along an arc (10) as the suspension arm is turned so that the beam (3, 3') constantly hits the tangent of the arc (10) of the supporting point (99, 99') in a perpendicular direction. In that case the area to be imaged is the centre (9, 9') of the arc (10). According to the invention, the direction of rotation of the imaging means (2, 2', 4, 4') would be changed during the imaging scan (11) according to the requirements set by the object to be imaged.

The above examples describe use of the invention mainly in odontological x-ray photography. However, these solutions described as preferred embodiments do not limit applicability of the invention to the embodiments according to the examples, but the scope of protection is defined by the following claims, within which several details of the inventive concept may vary. The invention can also be utilized for imaging not based on the use of x-radiation and in connections other than odontology. In fact, the invention is applicable to all cases where it is preferable to use a digital CCD (charge coupled device) sensor as the detector and e.g. TDI or frame transfer techniques for reading it (as regards the techniques which are known per se, reference is made to Finnish application 955598, for example), because the invention allows to use the same small and thus economical sensor in the same device. In the field of medicine, for example, the invention enables use of the same device for panoramic imaging of the dental arc and imaging of other kinds of the cranial area and allows to produce different cross-sectional and longitudinal images.

What is claimed is:

1. A method in tomographic imaging, in which the object to be imaged is preferably held in place and a receptor located substantially on an opposite side of the object to be imaged receives radiation of a beam from an electromagnetic radiation source, wherein the radiation source and the detector are moved in a controlled manner substantially on the opposite sides of the object to be imaged for moving the beam in the object to be imaged so that at least part of said movement is rotational movement with respect to the object to be imaged, and further wherein at least part of the tomographic effect is produced by scanning the object to be imaged with the beam so that during the scan the direction of rotation of the beam is at least once turned in the opposite direction in the object to be imaged.

2. A method according to claim 1, wherein the rotational direction is changed constantly to and fro at least over a section of the scan.

3. A method according to claim 1, wherein the rotational direction is changed 1 to 5 times as the beam scans a distance corresponding to its width in the object to be imaged.

4. A method according to claim 1, wherein the rotational direction is changed 1 to 10 times during the scan.

5. A method according to claim 1, wherein the radiation source and detector are moved so that the path of the area to be imaged is substantially linear in the object to be imaged.

6. A method according to claim 1, wherein the radiation source and detector are moved so that at least a section of the path of the area to be imaged in the object to be imaged substantially has the shape of an arc, circle, letter S, chevron pattern or a combination of some of these.

7. A method according to claim 1, wherein the paths of the radiation source and detector with respect to the object to be imaged comprise horizontal sections, vertical sections, or combinations of these and/or sections parallel with the beam.

8. A method according to claim 1, wherein the radiation source and detector are moved substantially along paths needed to obtain a panoramic image of a cranial area.

9. A method according to claim 8, wherein the cranial area includes a dental arc, and to produce a panoramic image of the dental arc, the rotational direction is changed as the beam travels from the area of a temporomandibular joint to the area of the dental arc and/or from the area of the dental arc to the area of the temporomandibular joint.

10. A method according to claim 9, wherein the radiation source and detector are moved substantially along the paths which produce a cross-sectional or longitudinal image of the cranial area.

11. A method according to claim 1, wherein x-radiation is used as the electromagnetic radiation.

12. A method according to claim 1, wherein the beam used is substantially narrower than the object to be imaged.

13. A method according to claim 1, wherein a digital sensor is used as the detector and TDI or frame transfer technique is used for reading the sensor.

14. A method according to claim 1, wherein changes of the beam incidence angle and/or propagation speed in the object are compensated for with changes of the radiation detection speed.

15. A method according to claim 14, wherein the radiation detection speed is maintained constant and the change of the beam incidence angle in the object is compensated for by changing the beam scanning speed in the object.

16. A tomographic method of producing a cross-section or longitudinal image of the cranial area, in which the object to be imaged is preferably held in place and a receptor located substantially on the opposite side of the object to be imaged receives radiation of a beam from an X-ray radiation source, wherein the radiation source and the detector are moved in a controlled manner substantially on the opposite sides of the object to be imaged for moving the beam in the object to be imaged so that at least part of said movement is rotational movement with respect to the object to be imaged, and further wherein at least part of the tomographic effect is produced by scanning the object to be imaged with the beam so that during the scan the rotational direction of the beam is changed 1 to 5 times as the beam scans a distance corresponding to its width in the object to be imaged.

17. An apparatus for tomographic imaging, the apparatus comprising a radiation source for generating an electromagnetic beam, a radiation detector, means for placing the object to be imaged substantially between the radiation source and the detector; and means for moving the radiation source and the detector in a controlled manner during an image scan in a rotational direction on opposite sides of the object to be imaged and during the imaging scan, moving the radiation source and detector at least once in an opposite rotational direction.

18. An apparatus according to claim 17, wherein the means for moving are mechanical.

19. An apparatus according to claim 18, wherein the radiation source and detector are attached substantially to the opposite ends of the common suspension arm, and wherein the means for moving consist of guide tracks or other means for moving the suspension arm so that the arm can be moved along a path which is substantially parallel with a cross section produced from the object to be imaged, but comprises at least one S curve.

20. An apparatus according to claim 17, the means for moving consists of at least one electric motor which moves the imaging means, and means for controlling the motor.

21. An apparatus according to claim 1, wherein said means for moving includes means for changing the rotational direction constantly to and fro at least over a section of the whole scanning motion.

22. An apparatus according to claim 17, wherein said means for moving includes means for changing the rotational direction 1 to 5 times as the beam scans a distance corresponding to its width in the object to be imaged.

23. An apparatus according to claim 1, wherein said means for moving includes means for changing the rotational direction 1 to 10 times during the whole imaging scan.

24. An apparatus according to claim 1, wherein said means for moving includes means for moving the radiation source and detector so that the path of the area to be imaged is substantially linear in the object to be imaged.

25. An apparatus according to claim 1, wherein said means for moving includes means for moving the radiation source and detector so that at least part of the path of the imaging area in the object to be imaged substantially has the shape of an arc, circle, letter S, chevron pattern or a combination of some of these.

26. An apparatus according to claim 1, wherein said means for moving includes means for arranging the paths of the radiation source and detector with respect to the object to be imaged so that they comprise horizontal sections, vertical sections or combinations of these and/or sections parallel with the beam.

27. An apparatus according to claim 1, wherein said means for moving includes means for moving the radiation source and detector substantially along paths need to obtain a panoramic image of a cranial area.

28. An apparatus according to claim 27, wherein the cranial area includes a dental arc and said means for moving includes means for changing the rotational direction as the beam travels from the area of a temporomandibular joint to the area of the dental arc and/or from the area of the dental arc to the area of the temporomandibular joint.

29. An apparatus according to claim 27, wherein said means for moving includes means for moving the radiation source and detector substantially along paths needed to obtain a cross-sectional or longitudinal image of the cranial area.

30. An apparatus according to claim 1, wherein the source of electromagnetic radiation is an X-ray tube.

31. An apparatus according to claim 1, including means for defining the beam so that it is substantially narrower than the object to be imaged.

32. An apparatus according to claim 1, wherein the detector is a digital sensor.

33. An apparatus according to claim 1, including means for compensating for changes of the beam incidence angle and/or propagation speed in the object with the changes of the radiation detection speed.

34. An apparatus according to claim 1, includes means for maintaining the radiation detection speed constant and means for compensating for the change of the beam incidence angle in the object with the changes of the beam scanning speed in the object.

35. An apparatus for producing cross-sectional or longitudinal tomographic images of the cranial area, the apparatus comprising a radiation source for generating an electromagnetic beam, radiation detector, means for placing the object to be imaged substantially between the radiation source and the detector; and means for moving the radiation source and the detector in a controlled manner during an imaging scan in a rotational direction on the opposite sides of the object to be imaged, such that, during the imaging scan, the rotational direction of the beam changes 1 to 5 times in the object as the beam scans a distance corresponding to its width in the object to be imaged.

36. An imaging mode in a panoramic x-ray apparatus, which comprises a radiation source for generating an x-ray beam, radiation detector, means for placing the object to be imaged substantially between the radiation source and the detector; and means for moving the radiation source and the detector in a controlled manner during an imaging scan in a rotational direction on the opposite sides of the object to be imaged such that the rotational direction of the radiation source and detector turns at least once during the imaging scan in an opposite direction with respect to the object to be imaged.

* * * * *